United States Patent [19]

Kessler

[11] Patent Number: 4,898,181

[45] Date of Patent: Feb. 6, 1990

[54] METHOD OF ILLUSTRATING ELECTROCARDIOGRAPHIC VALUES

[76] Inventor: M. Kessler, Waldstrasse 6, D-8520 Erlangen, Fed. Rep. of Germany

[21] Appl. No.: 262,107

[22] Filed: Oct. 19, 1988

Related U.S. Application Data

[63] Continuation of Ser. No. 919,751, Oct. 14, 1986, abandoned.

[30] Foreign Application Priority Data

Oct. 15, 1985 [DE] Fed. Rep. of Germany ....... 3536658

[51] Int. Cl.⁴ .............................................. A61B 5/04
[52] U.S. Cl. ..................................... 128/699; 128/710
[58] Field of Search ................................ 128/695–696, 128/699, 710–712; 364/413.05–413.06

[56] References Cited

U.S. PATENT DOCUMENTS

| | | | |
|---|---|---|---|
| 3,884,221 | 5/1975 | Eastman | 128/699 |
| 4,101,961 | 7/1978 | Reiber | 128/695 X |
| 4,204,225 | 5/1980 | Mistretta | 128/695 X |
| 4,478,223 | 10/1984 | Allor | 128/699 |
| 4,569,357 | 2/1986 | Sanz et al. | 128/699 |
| 4,570,225 | 2/1986 | Lundy | 128/710 X |
| 4,637,400 | 1/1987 | Marcus | 128/695 X |
| 4,639,223 | 1/1987 | Keler | 128/695 X |
| 4,674,518 | 1/1987 | Salo | 128/695 |

FOREIGN PATENT DOCUMENTS

| | | | |
|---|---|---|---|
| 2409173 | 9/1975 | Fed. Rep. of Germany | 128/695 |
| 2447396 | 4/1976 | Fed. Rep. of Germany | 128/695 |

*Primary Examiner*—Angela D. Sykes
*Attorney, Agent, or Firm*—Michael J. Striker

[57] ABSTRACT

In order to increase the evaluability of electrocardiographic values, the signals which are indicatable in a method for illustrating electrocardiographic values which are shunted off by shunting off electrodes and by amplifiers and indicating means, which are associated with the shunting off electrodes, are timely recorded in intervals which are small with respect to the total cycle, digitalized and fed to a computer for calculating of coordinates which describe the excitation expansion and that these coordinates are analytically supplemented into layer faces or layer lines and are recorded as a metamorphic process in a graphic heart model in such a manner that the excitation process is visible in the heart model.

12 Claims, 7 Drawing Sheets

METHOD OF ILLUSTRATING ELECTROCARDIOGRAPHIC VALUES

This application is a continuation of application Ser. No. 919,751, filed Oct. 14, 1986, now abandoned.

The invention relates to a method for illustrating electrocardiographic measuring values which are shunted off by means of shunt off electrodes and which values amplified by amplifiers which are associated with the shunt off electrodes and indicated by indicator means, as well as a device for illustrating electrocardiographic measuring values consisting of shunt off electrodes, amplifiers associated with the shunt off electrodes and indicator devices.

The electrocardiography is an important method for measuring heart activity by measuring the electrical potentials generated during the movement of the heart muscle.

The evaluation of the electrocardiographically obtained values, which are mostly present in form of continuously extending curves is an established method of diagnosis, but hitherto it had the disadvantage that the curves showed a more or less abstract interrelation with the contraction of the hollow muscle. This is caused because the electrical signal is at its largest when the electrical dipol, formed by the muscle, reaches its maximum value namely all fibers of the muscle. This condition is present mostly when the spatial widening of the contraction is progressed to about the center of the muscle. There, it has the percentage largest expansion.

Therefore, the activity signal corresponds to about the differential quotients of the contraction. However, it would be desirable to obtain a magnitude which corresponds to the spatial expansion of the contraction.

An example for the high information content of the electrical measuring of the heart activity and simultaneously a difficult evaluation is the vector electrocardiogram.

SUMMARY OF THE INVENTION

It is an object of the present invention to provide an illustration of the activity of the heart muscle, which depends only from the measured electrical potentials, on the one hand, and also results in a picture of the spatial expansion of the contraction in the muscle, on the other hand.

This object is attained by a method in which the signals are recorded timely in intervals which are small with respect to the total cycle, then the signals are digitalized and fed to a computer for calculating the coordinates describing the excitation widening, these coordinates being analytically supplemented into layer faces or layer lines and entered as a metamorphic process into a graphic heart model in such a manner that the excitation process is visible in the heart model.

Such a solution is advantageous in that an integration of the signals of the muscle activity is performed, so that the spatial excitation process is automatically obtained from the actual electrical muscle activity and that therefore the recording of the layer lines and the layer faces in the graphic heart model permits the simple observation and assessment of the excitation expansion in the heart muscle.

The device for carrying out this illustration includes shunt off electrodes, and associated amplifiers which are provided with indicator means, whereby the signals of the shunt off electrodes are fed digitally to a computer in which the coordination of the excitation process is calculated and subsequently the calculated coordinates are fed to an indicator device on which, at the same time, a graphic heart model is permanently illustrated.

In detail, the heart model is illustrated in form of a three dimensional wire model or contour model into which the layer lines or layer faces of the excitation expansion are entered, whose spatial position is determined by the given calculated electrical main vector and whose distance with respect to each other is determined by the magnitude of the main vector.

Thus, the total content of the required measurements for a vector cardiogram is evaluated, but illustrated in a form which makes the excitation process immediately visible.

In particularly complicated processes or for purposes of demonstration it may be advantageous if the the heart model is illustrated in a plurality of two-dimensional sections.

In a further development of the method the signals of the shunt off electrodes are stored in a storage medium, for example, a magnetic plate, they can be called from the same by the computer and after calcuating the illustrated coordinates can be illustrated on an indicator device.

The advantage of this further development resides in that an off-line operation of the indicator device is made possible requiring lower calculating speeds for calculating the layer lines or layer faces, on the one hand, and that it is further possible to follow the excitation expansion either in slow motion, in that the slow creation of the layer planes or layer lines of the excitation expansion is observed or to evaluate the layer line model as a while, whereby the distance of the layer lines characterize the time process and whereby the incline of the layer planes corresponds to the direction of the main vector.

Thereby, the great superiority of the direct indicating method is shown with respect to the more abstract methods of the customary electro or vector diagrams.

Instead of an isovolumetric illustration with layer lines or layer planes, the contraction condition may also be shown by a color filling of the heart model in that a main vector is calculated and in that the main vector defines the further progress of the color filling of the model.

Advantageously, different colors are used for illustrating the layer faces in order to differentiate the excitation process in the atricles from the ventricles. Also when illustrating the layer faces themselves different colors or shadings may be used for improving the differentiation of lower side and upper side of the layer faces.

An improved illustration of the excitation process is obtainable in that one each vector is associated with one each anatomic element of the model, so that additional details of the contraction process can be obtained and illustrated.

However, it is a prerequisite to provide a corresponding specific shunting off of the action potential. This can be obtained by means of shunting off electrodes which are disposed directly on the muscle. It may also be determined by means of two frontally and dorsally disposed shunt off electrodes which are termed "scanning electrodes" which preferably are penetrated by the electric heart axis and whereby the electroactivity signals between one each frontal and dorsal electrode of the two scanning electrodes are sequentially or simultaneously measured.

In an illustration which had been shunted off in such a manner one individual vector must be associated with each pair of electrodes. Thereby, not only an idealized two-dimensional layer face can be illustrated as an expansion front, but also the layer face is further broken up and a three-dimensional layer face is generated.

An other further development of the invention consists in that the anatomic elements of the model, for example, the spatial expansion of the auricles and chambers, the muscle volume, the location of excitation sags or of excitation sources are adjustable spatially and/or timely in the model. Thereby it is possible not only to shape the muscle model in the form of a phantom model of the heart muscle, but however to adapt the same to the actually measured data.

A further development of this method consists in that a selfexcitable, illustratable heart phantom shaped as a computer program is passed through by a computer being adaptable to the given measured electrocardiographic values by changing the anatomic phantom parameters, like muscle volumes, excitation sources, excitation sags, nerves, expansions of the anatomic elements in such a manner that the simulated cardiogram is homomorpheously illustratable on the actually measured electro or vector diagram.

From the selection of the parameters which are illustratable such as amplitudes, frequencies, phases, time delays or timely jumps, information about the anatomical conditions on the actual muscle can be obtained.

A further adaptation to the actual excitation process can be performed in that the electrical model together with an actual picture of the heart muscle is illustratable on the same indicator device. Thus, the model parameters can also be adjusted to the actual muscle.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF THE PREFERRED EMBODIMENTS

Figure 1A:
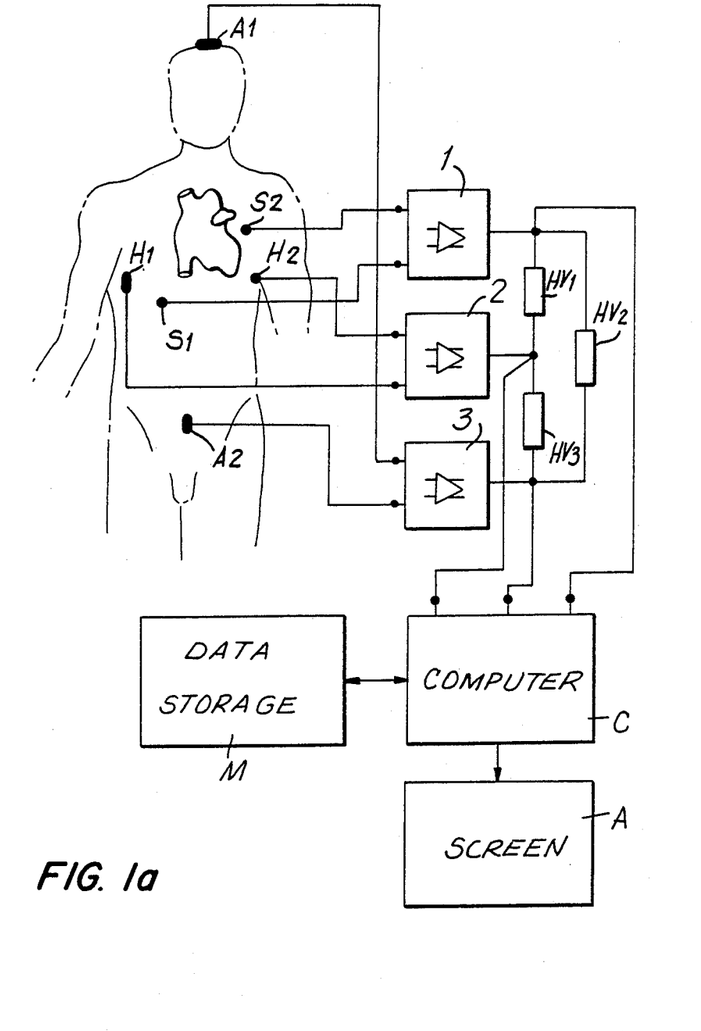
FIGS. 1a–c show a model of the measuring arrangement with points of application of scanning electrodes on a patient's body and illustrations of the heart model.

FIG. 1a illustrates the shunt off points A1,A2,S1,S2,H1,H2, which in the Preferred Embodiments may be used for picking up the electroactivity by means of sensing electrodes which are customary in the field of the invention. However, other known scanning or pick-up means may be used, if corresponding calculating routines are made available in an associated computer C for vector determination.

In the exemplified embodiment A1,A2 are the axial electrodes, H1,H2 are the horizontal electrodes and S1,S2 are the saggital electrodes. Their signals which are amplified by amplifiers 1,2,3 are considered in the hitherto known manner as orthogonal vectors HV1, HV2, HV3 and are combined into a main vector HV in the electronic computer C.

Figure 1B:
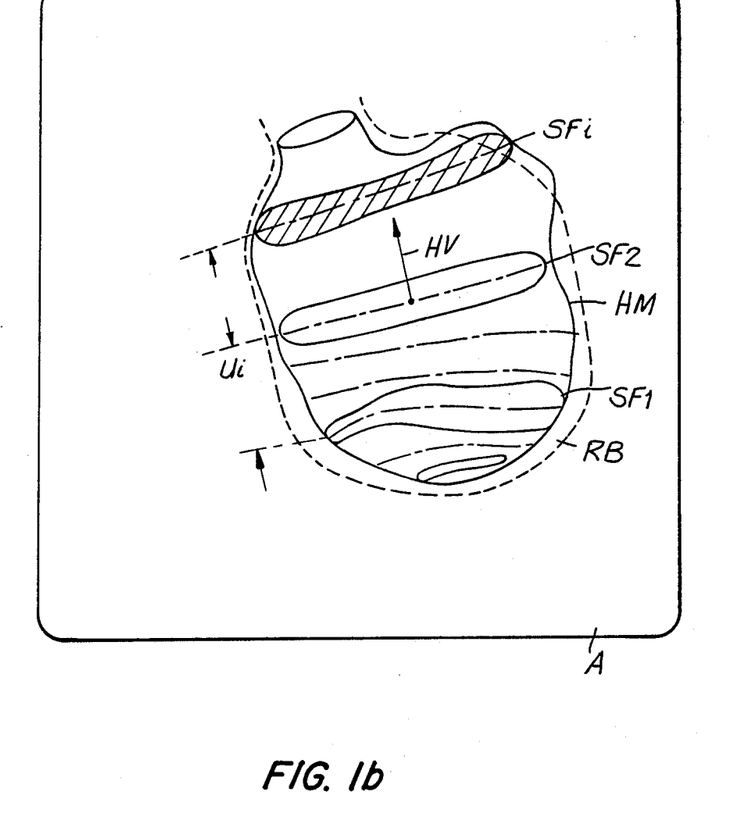

In accordance with the invention this main vector is no longer illustrated as a single vector or as an end point two dimensionally, but it is used as a normal of a layer face or sectional area, for example, the layer face SF1 in a heart model HM being permanently illustrated on a screen A (FIG. 1b).

The illustration of the normal may be eliminated if instead of the vector magnitude the distance Ui between the layer faces is adjusted, for example. In this case a layer line picture is generated from these to be recorded layer faces SF1, SF2, . . . SFi, the distances U1,U2, . . . between which are determined by the magnitude of the given main vector HV.

The illustration of the layer faces (SF1, SF2, . . . ) may be improved in that the given visible face is characterized as an upper face or lower face by specific face patterns.

Figure 1C:
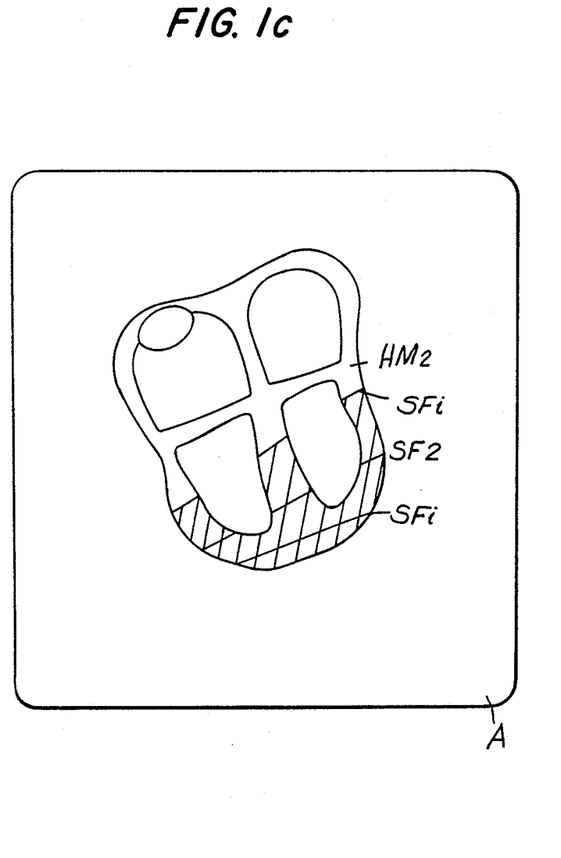

In specifically complicated procedures individual face segments HM2 maybe illustrated in accordance with FIG. 1c in a heart model and the measured or calculated excitation fronts (SF1,SF2 . . . ) may be entered into the model.

In any case the values obtained either by measuring technique or by calculation are stored in a data storage M of computer C (FIG. 1).

Figure 2A:
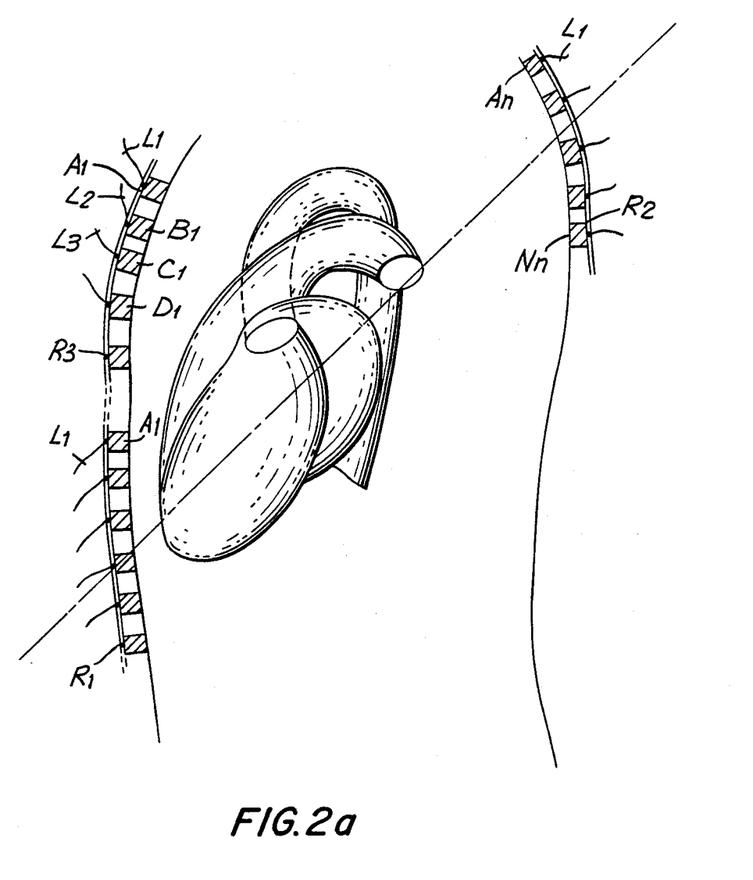
FIGS. 2a–c show scanning electrodes for a more accurate measuring technical determination of excitation fronts and main vectors.
Figure 2B:
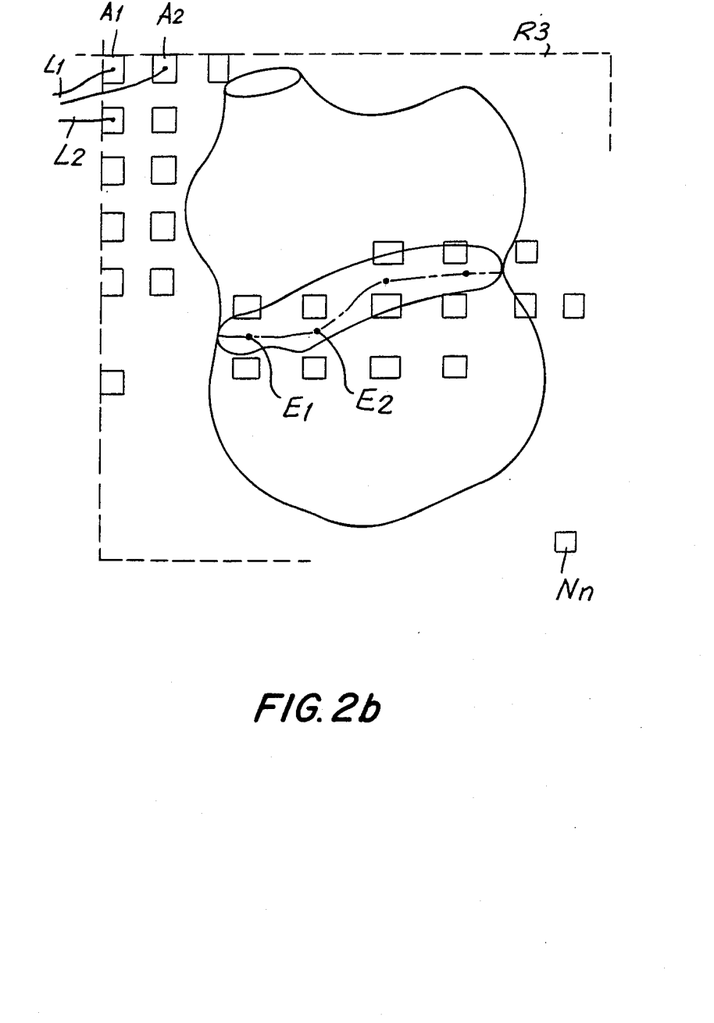
Figure 2C:
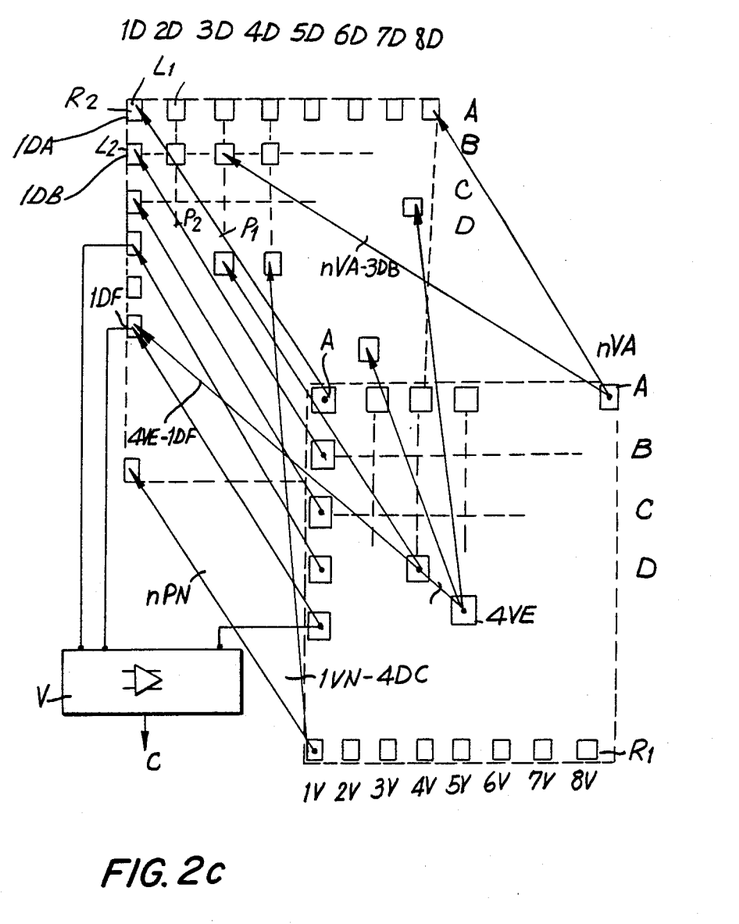

An improvement of the illustration may be obtained, if in accordance with FIG. 2 a combined network of scanning or pick-up electrodes A1, A2, . . . Nn in form of "array or grating electrodes" R1,R2,R3 are mounted frontally and/or dorsally above the heart muscle.

The known unipolar WILSON-lead may be used with a frontal mounting of a single scanning electrode (R3) on a cross-section of a maximum projection of the heart muscle on the chest wall. Thereby, the electrodes A1, A2 . . . Nn, which are connected with lines L1,L2 . . . to the amplifiers (not shown) are measured against the collector electrode (not shown), so that in accordance with FIG. 2b the process of the excitation front E1,E2, . . . can be determined by seeking the given maximum signals from the A1 . . . .

If, in accordance with FIG. 2a, two scanning electrodes R1, R2 are mounted frontally and dorsally in such a manner that the heart axis extends through the scanning electrodes, then the different section vectors may be determined in accordance with FIG. 2c as follows: the "parallel vectors" extending parallel to the heart axis 1PA . . . 1PN or "bundle vectors" 4VE-1DF (central bundle vector) nVA-3DB (right apical bundle vector) 1VN-4DC (left apical bundle vector)

From these individual vectors the given maximum vector present can be determined by the computer C by selecting the signals from all measuring channels of amplifier V.

Since the muscle activity substantially extends in the direction of the heart axis a good measuring technically determined approximation of the actual process of the excitation expansion can be already found with this process.

The measuring itself is controlled by the electronic computer C and is performed in intervals which are small with respect to the total cycle of the muscle. Thereby, the digital values of the electrode signals are used for calculating the main vector HV, or the computer C performs the selection of the maximum vector. The obtained data is preferably stored in the data storage M of computer C.

The mode of the illustration in accordance with the invention will be now explained in detail. Two instantaneous pictures are illustrated on the same indicator device or screen of FIG. 1b: One picture of the heart phantom Hm and a contour model RB of the actual muscle. Thereby, the actual picture RB has been taken, for example, by a camera during transillumination with radioscopy, while the phantom picture HM is internally generated by the computer C.

If a series of a plurality of actual pictures RB and heart models HM are taken successively, it can then be compared whether the excitation process in the phantom picture HM and the contraction in the actual picture RB are in conformity with each other. Thus a first indication is obtained of the actual activity distribution processes in the heart muscle, since the measuring of the actual electrical heart activity is the basis for the phantom picture.

Figure 3:
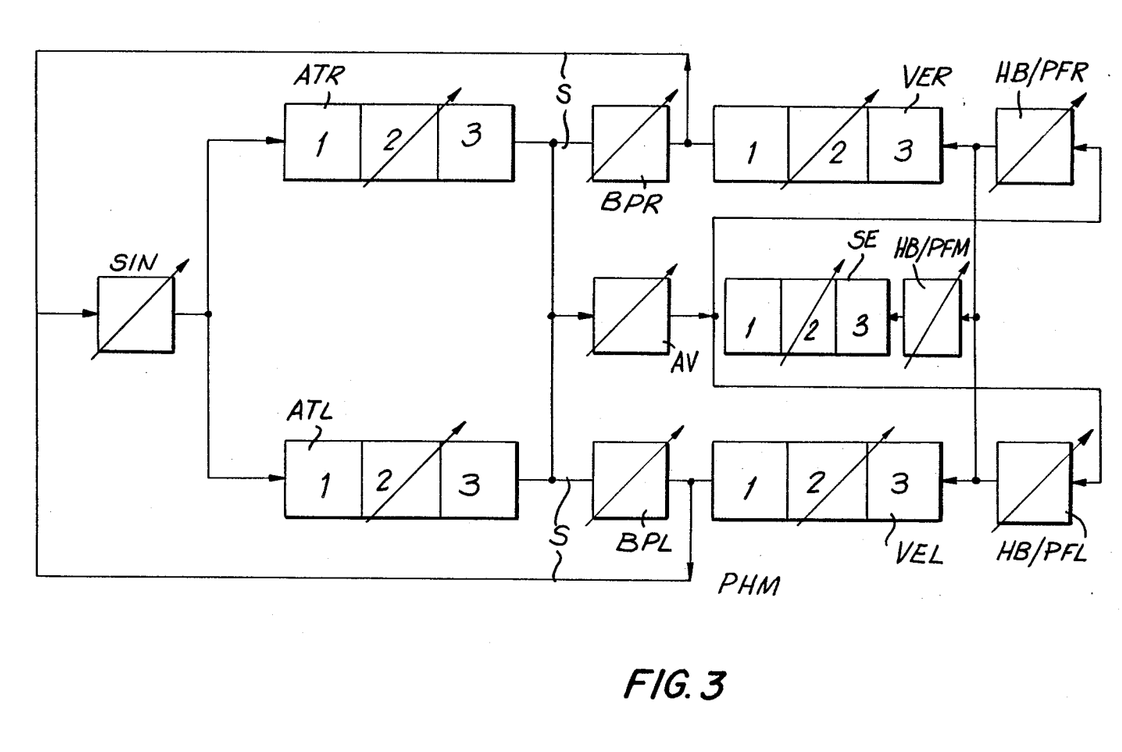
FIG. 3 illustrates a phantom model of the heart muscle.

Another type of analysis can be performed in that a self-excited phantom heart PHM is simulated in the computer C, FIG. 3, which composes its excitation process from elements corresponding to the three-dimensional auricular activities (ATL,ATR-1/2/3), the three-dimensional ventricular activities (VEL,-VER,SE-1/2/3), the effectivity and the volume of the muscle parts (amplitude factors) and on which excitation sags (weakening in HB/PFL,HB/PER) or excitation sources (autonomic sources, BPL,BPR, for example, infarct scars) can be imprinted.

Thus, a complete autonomic oscillating program technical equivalent of a heart muscle is obtained, whose parameters are individually open and which are in conformity with the actual muscle and its behavior, after the excitation processes of the phantom model and the actual muscle are adjusted with respect to each other.

The adaptation of the parameters of the phantom model PHM is performed as long, for example, as the measured EKG-values of the actual muscle, which are illustrated as a curve, are in conformity with the synthesized process in the phantom model with one of the customary methods of shunting off of the action potential.

The process of a phantom cycle is as follows: An autonomous oscillating excitation center SIN triggers an excitation process in the auricles ATL, ATR, which is controllable in three coordinates (1,2,3) in accordance with amplitude and time. Thereby, the total process—depolarisation, repolarisation—is simulated. In view of this first process a further excitation process is triggered through AV being fed through lines HB/PFL and HB/PFR to the ventricles VEL,VER and there it triggers an excitation process (with reversed electrical polarity).

After completion of this process a new cycle is again triggered by the autonomic center SIN.

The equivalency of model PHM with respect to the heart muscle is obvious: The sinus knot (SIN) triggers the excitation process in the auricles (AVL,AVR) which trigger the excitation of the ventricle through the AV-knot and the HIS bundles and the Purkin-fibers (HB/PFR-PFL). The overlapping of local vectors with opposite expansion direction or of phase displaced excitation waves (depolarisation of one, repolarisation of the other muscle group) results in the known and characteristic partial cancellations of the electrical signals. Feedbacks of repolarisating muscle parts to the rhythm defining, selfexcitable element SIN can be realized by stray lines S.

All parameters (SIN, AVL, AVR, AV, VEL, VER, HB/PFL, HB/PFR, HB/PFM, BPR, BPL) of this simulation are adjustable in accordance with amplitude in three coordinates (1,2,3), in accordance with excitation threshold and time process. For example, they act against each other when the potentials resulting in different parts of the muscle caused by depolarisation or repolarisation compensate with respect to each other totally or partially. However, this is the same situation as in the actual muscle. Now, the simulation permits the independent variation of the individual elements and also the independent individual illustration thereof, so that the individual processes are visible and that thereby substantial knowledge is made possible concerning the actual processes.

I claim:

1. A method of recording electrocardiographic values of an actual heart muscle, comprising the steps of applying scanning electrodes to predetermined locations of a patient's body, picking up electric signals delivered by said electrodes at time intervals which are small with respect to a total cycle of the heart muscle; amplifying the pick-up signals, and converting the same into digitalized vector data; feeding the vector data into a computer programmed for computing from the vector data coordinate values of discrete sectional planes SF1,SF2 . . . ) of the heart muscle superimposed at distances; computed from the vector data during the heart muscle cycle; and graphically displaying at said time intervals changes of said superimposed planes to provide a live heart model (HM) showing the expansion processes of the heart muscle.

2. A method in accordance with claim 1 wherein said electrodes include axial (A1,A2 . . . ), horizontal (H1,H2 . . . ) and saggital (S1,S2 . . ) electrodes, and the signals from said electrodes are converted into digitalized data corresponding to orthogonal vectors of the heart muscle activity which are combined into a main vector in the computer.

3. A method in accordance with claim 1, wherein the heart model is displayed as a three dimensional contour model on an indicating device (A) on which expansion of the planes (SF1,SF2 . . . ) are recorded, and a position of each of said planes being determined by the calculated growth of a main vector (HV) and the distance thereof from the preceding plane.

4. A method in accordance with claim 1, wherein the heart model is illustrated in two-dimensional sections (HM2) on an indicating device (A).

5. A method in accordance with claim 1, wherein the signals of the scanning electrodes (A1,L1, . . . Nn) are digitally stored and may be called by the computer (C) and after calculating the sectional planes thereof (SF1,SF2 . . . ) they are displayed on an indicating device (A) together with said live heart model (HM).

6. A method in accordance with claim 1, wherein the computer (C) calculates a main vector (HV) of the muscle activity and that the main vector defines the color fill of said live heart model (HM2).

7. A method in accordance with claim 1, wherein program technical elements (ATL,ATR,,,1/2/3) of a phantom heart model (PHM) correspond to anatomical elements of the actual muscle; each of said program technical elements generating three orthogonal vectors, whose spatial and time parameters are variable; and for each conductive element of the heart muscle a timely variable program technical line element of the model (PHM) is provided.

8. A method in accordance with claim 7, wherein electro/vector cardiograms of the phantom heart model and of the actual heart muscle are illustrated simultaneously and superimposed on an indicating device (A).

9. A method in accordance with claim 8, wherein in addition to the cardiograms the live heart model (HM) is illustrated on the indicating device (A).

10. A method in accordance with claim 8, wherein the differences of the course of the program technical elements (ATL,ATR, . . . ) are measured between the phantom model (PHM) and the actual heart muscle and are used for controlling the program technical elements (ATR,ATL . . . ) in such a manner that the deviations between the actual and the simulated measured values are eliminated.

11. A method in accordance with claim 10, wherein the geometric measurements of the heart model (HM) are varied in correspondence to the variation of the program technical elements (ATR,ATL . . . ) of the phantom model (PHM).

12. A method in accordance with claim 1, wherein the live heart model (HM) is illustratable on the same indicating device (A) together with an X-ray photograph (RB) of the heart muscle.

* * * * *